United States Patent [19]

Verbeek et al.

[11] Patent Number: 5,028,727

[45] Date of Patent: Jul. 2, 1991

[54] PLATINUM-(IV)-DIAMINE COMPLEX

[75] Inventors: Francois Verbeek, Hamelen; Harmen A. Meinema, Leusden, both of Netherlands

[73] Assignee: Nederlandse Organisatie Voor Toegepast-Natuurwetenschappelijk Onderzoek Tno, Hague, Netherlands

[21] Appl. No.: 386,881

[22] Filed: Jul. 31, 1989

[30] Foreign Application Priority Data

Aug. 31, 1988 [NL] Netherlands .......................... 8802149

[51] Int. Cl.$^5$ .............................................. C07F 15/00
[52] U.S. Cl. ................................................... 556/137
[58] Field of Search ........................................ 556/137

[56] References Cited

U.S. PATENT DOCUMENTS 4,431,666  2/1984  Bulten et al. ........................ 514/492

FOREIGN PATENT DOCUMENTS 8302115   6/1983  Netherlands .
2024823A  1/1980  United Kingdom .
2066819A  7/1981  United Kingdom .
2128615A  5/1984  United Kingdom .

Primary Examiner—Merrell C. Cashion, Jr.
Assistant Examiner—G. S. Kishore
Attorney, Agent, or Firm—Bachman & LaPointe

[57] ABSTRACT

The invention relates to a platinum-(IV)-diamine complex of the formula:

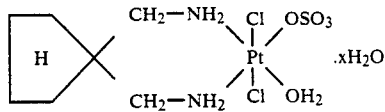

to a method for the preparation of said compound and to a preparation with an antitumor action containing said compound. Further said preparations with an antitumor action containing said compounds are disclosed.

1 Claim, No Drawings

PLATINUM-(IV)-DIAMINE COMPLEX

The invention relates to a platinum-(IV)-diamine complex and to a method for the preparation of this compound, to a preparation with an anti-tumour action which contains a compound a compound of this type and to shaped preparations with an anti-tumour action.

About twenty years ago the American biochemist B. Rosenberg discovered that cis-diamine-dichloro-platinum (cis-platinum) exhibits a very strong anti-tumour activity; B. Rosenberg, L. van Camp, J. Trosko and V. H. Mansour, Nature 222, (1969) pages 385-386. In the meantime this compound, in combination with other anti-tumour agents, has found important applications in the treatment of tumours, in particular of the ovary and testes. Cis-platinum has, however, a number of highly undesirable side effects. It causes severe nausea in the patient, in combination with vomitting. In addition, it displays kidney, bone marrow and neurotoxicity and can cause damage to the hearing. Reference is made here, for example, to the article by D. Th. Sleijfer, S. Meijer and M. H. Mulder, Cis-platin: a review of clinical applications and renal toxicity. Pharm. Weekbl. [Sci.] 1985; 7: pages 237-244. Since the start of the nineteen seventies, a great deal of research has also been carried out world-wide on the mechanism of action of cis-platinum and on the development of analogues with a higher anti-tumour activity and/or activity against tumours not susceptible to date, analogues with reduced toxic side effects and/or analogues with improved physical and pharmacological properties.

Numerous platinum-diamine complexes are known from the literature. However, there is still a great need for new anti-tumour agents with improved characteristics, specifically for compounds with activity against tumours which are resistant or have developed resistance to cis-platinum. Reference is made here, for example, to two recent review articles and to the literature references mentioned therein; E. W. Stern, The Search for New Platinum Antitumor Agents: Progress, Problems and Prospects, in Platinum and other Metal Coordination Compounds in Cancer Chemotherapy, Edited by Marino Nicolini, Martinus Nijhoff Publishing, Boston, Dordrecht, Lancaster, ISBN No. 0-89838-358-7, 1988, pages 519-526; H. A. Meinema, Platinaverbindingen ter bestrijding van kanker: synthese, eigenschappen en structuur-activiteitsrelaties (Platinum compounds for combating cancer: synthesis, characteristics and structure-activity relationships) Pharm. Weekbl., 123 (1988) pages 549-552.

Diamine-platinum complexes are described in Dutch Patent Application No. 79.04740 which are characterized by the formula 1 on the sheet of formulae, where $R_1$ and $R_2$ independently of one another represent a hydrogen atom or a substituted or unsubstituted alkyl, cycloalkyl, aryl or aralkyl group, while $R_1$ and $R_2$ together with the carbon atom to which they are bonded can be a substituted or unsubstituted cycloalkyl group, $R_3$ and $R_4$ independently of one another represent a hydrogen atom or a substituted or unsubstituted alkyl, aryl or aralkyl group and X represents an anionic group.

Diamine-platinum complexes are known from Dutch Patent Application No. 82.04067

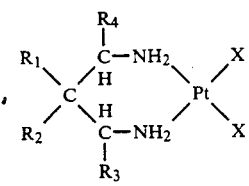

FORMULA 1 which are characterized by the formula 1 as set out herein below wherein $R_1$ and $R_2$ both represent an ethyl group or, together with the carbon atom to which they are bonded, a phenyl group (it is pointed out here that the examples indicate that it is not a phenyl group but a cycloalkyl group which is meant), $R_3$ and $R_4$ both represent a hydrogen atom and each X represents a chloroacetate or nitrate group, or both groups X together represent a malonate group, an ethylmalonate group, a hydroxymalonate group, a carboxyphthalate group, a cyclobutane-1,1-dicarboxylate group or an oxylate group, or a sodium salt of one of these groups.

Extensive research carried out by the National Cancer Institute, Bethesda, USA and the European Organization for Research on the Treatment of Cancer, Brussels, Belgium, has shown that these compounds exhibit a high therapeutic activity against cancer. In comparison with other platinum complexes for combating cancer which are known and are used in practice, these complexes have a lower kidney toxicity.

Platinum complexes with an anti-tumour action are known from Dutch Patent Application No. 80.0032, now patent No. 181.434, which have the formula 2 as set out hereinbelow

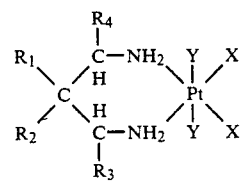

FORMULA 2 wherein $R_1$ and $R_2$ independently of one another represent a hydrogen atom or a substituted or unsubstituted alkyl, cycloalkyl, aryl or aralkyl group, while $R_1$ and $R_2$, together with the carbon atom to which they are bonded, can form a substituted or unsubstituted cycloalkyl group, $R_3$ and $R_4$ independently of one another represent a hydrogen atom or a substituted or unsubstituted alkyl or aralkyl group and X and Y represent identical or different anionic groups. These compounds also exhibit an action against a number of types of cancer and a reduced kidney toxicity.

It has now been found that the compound of the formula 3 as set out herein below

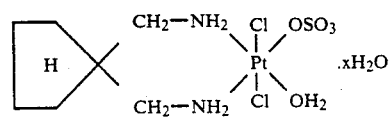

FORMULA 3

(TNO-40) has a surprisingly good action against tumour cells which have become resistant to cis-diamine-dichloro-platinum (cis-platinum).

The compound of formula 3 can be prepared by reacting a compound of formula 4 as set out hereinbelow with K₂PtCl₄, chlorinating the reaction product and reacting with silver sulphate.

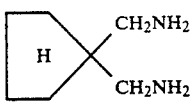

The compound of the formula 3 exhibits an outstanding action against diverse types of tumours. From experiments with tumour-carrying mice it appears that the survival time of treated mice (T) has increased significantly compared with that of the untreated mice (C). There is talk of significant therapeutic activity with a T/C×100% (T/C %) of greater than or equal to 125.

Against L1210 leukaemia the maximum T/C (%) is 193 (4 mg/kg), while in a control experiment cis-platinum achieves a maximum T/C (%) of 138 (6 mg/kg); against B melanoma the maximum T/C (%) is 163 (0.8 mg/kg), while cis-platinum achieves a maximum T/C (%) of 171 (1.6 mg/kg) and against M5076 sarcoma implanted s.c. (subcutaneously) and treated i.v. a maximum T/C (%) of 126 (3 mg/kg) is found, while cis-platinum gives a maximum T/C (%) of 135 (4 mg/kg).

It is particularly interesting that this compound (TNO-40) exhibits an anti-tumor action against cell lines (A2780/124 and 2780/DDP) of A2780 human ovary carcinoma which are resistant to cis-platinum. The criterion here is that the ratio of the cell growth inhibiting concentrations IC$_{50}$ A2780/124 or IC$_{50}$ A2780/DDP to IC$_{50}$ A2780≧4.0. For TNO-40 the ratios found here were 3.3 and 3.6 respectively. For cis-platinum the corresponding values are 10 and 12.6 respectively.

The active compound obtained can be processed to pharmacological preparations in a manner known per se. The conventional additives can be used here.

The active compound according to the invention can be prepared in a manner known per se. The preparation is illustrated in the following examples.

EXAMPLE Ia

Cis-dichloro-1,1-bis(aminomethyl)cyclopentane-platinum-(II)

35.5 g (0.086 mol) K₂PtCl₄ and 17.2 g 1,1-bis-(aminomethyl)cyclopentane di-HCl salt are dissolved in 200 ml distilled water.

The solution is warmed to 90°–95° C.

A solution of 6.9 g NaOH in 70 ml distilled water is added at a rate such that pH: ≦7 (final pH=7.5).

The solid substance formed is filtered off with suction and rinsed with distilled water (50 ml) and acetone (25 ml). The dried solid substance is taken up in 600–800 ml liquid NH₃. The insoluble fraction is filtered off. After evaporating the NH₃, the product is washed with 2N HCl (50 ml) and distilled water (100 ml).

Dried in dessicator over KOH.

Weight dry: 23 g (68%)

Elemental analysis: Calculated % by weight: C: 21.33, H: 4.09, N: 7.11. Found % by weight: C: 21.25, H: 4.13, N: 7.27.

'H-NMR spectrum in DMSO-d₆ (VARIAN T-60) (shifts in ppm relative to TMS) CH₂ (ring): 1.46, CH₂ (NH₂): 2.18, NH₂: 4.90 (satellites 4.30 and 5.55).

EXAMPLE Ib

Tetrachloro-1,1-bis(aminomethyl)cyclopentane-platinum-(IV)

3 g (0.008 mol) cis-dichloro-1,1-bis(aminomethyl)cyclopentane-platinum-(II) are suspended in 40 ml distilled water.

The suspension is warmed to 70° C., after which chlorine gas is passed in for 1 hour, with stirring.

The excess chlorine gas is removed by passing air through the reaction mixture (temperature =70° C.).

The reaction mixture is cooled and the solid substance is filtered off with suction, washed with distilled water and dried over KOH under reduced pressure.

2.6 g (73%) of yellow solid substance are obtained.

Elemental analysis: Calculated % by weight: C: 18.08, H: 3.47, N: 6.02. Found % by weight: C: 18.06, H: 3.46, N: 6.14.

'H-NMR spectrum in DMSO-d₆ (VARIAN T-60) (shifts in ppm relative to TMS) CH₂ (ring): 1.50, CH₂ (NH₂): 2.23, NH₂: 6.80 (satellites 6.33 and 7.20).

EXAMPLE Ic

Cis-sulphato-trans-dichloro-1,1-bis(aminomethyl)cyclopentane-platinum-(IV)

3.5 g (0.0075 mol) tetrachloro-1,1-bis(aminomethyl)cyclopentane-platinum-(IV) are suspended in 110 ml distilled water. 2.21 g (0.007 mol) of silver sulphate are added to this suspension and the mixture is stirred for 24 hours with exclusion of light.

The AgCl formed is filtered off and rinsed with distilled water (20 ml).

The clear yellow filtrate is evaporated under reduced pressure. 3.0 g (81%) yellow solid substance are obtained.

Elemental analysis: Calculated % by weight. 2H₂O: C: 15.98, H: 3.83, N: 5.32, Pt: 37.07, Cl: 13.47, O: 18.24, S: 6.09. Founds % by weight: C: 16.05, H: 3.94, N: 5.35, Pt: 36.99, Cl 13.65, O: 18.08, S: 6.09.

'H-NMR spectrum in D₂O (VARIAN T-60) (shifts in ppm relative to the Na salt of trimethylsilylpropanesulphonic acid) CH₂ (ring): 1.63, CH₂ (NH₂): 2–2.6, H₂O/D₂O: 4.73.

Determination of the biological action of the compound prepared above.

In vitro Cytotoxicity

The cytotoxic action of the platinum complex was evaluated in vitro in a cell line panel consisting of B16-F10 murine melanoma, HCT-116 human colon carcinoma, A2780 human ovary carcinoma and 2 sub-lines of A2780 which are resistant to cis-platinum. The B16-F10 cell line was kept in a culture of Eagle's Minimum Essential Medium (MEM) with Earle's salts (Gibco) enriched with 2 mmol L-glutamine, 2.06 mmol sodium pyruvate, insulin (0.26 units/ml), penicillin/streptomycin (10 units/ml and 10 mcg/ml respectively), MEM non-essential amino acids (0.6% by weight Gibco) and 10% by weight foetal bovine serum (Hyclone). The HCT-116 cells were cultured in McCoy's 5A medium (modified Gibco) which was supplemented with 2 mmol L-glutamine, 0.12 mmol L-serine, 0.17 mmol asparagine, 1.5 mmol sodium pyruvate, MEM essential amino acids (0.625% by weight, Gibco), MEM non-essential amino acids (0.67% by weight, Gibco), MEM vitamins (0.6%, Gibco), foetal calf serum (10% by weight, Hyclone) and penicillin/streptomycin (10 units/ml and 10 mcg/ml respectively). The A2780 cell lines are cultured in RPMI medium 1640 (Gibco Laboratories) supplemented with foetal calf serum (10% by weight, Hyclone), 2 mmol L-glutamine and penicillin/-streptomycin. All cell lines were incubated at 37° C. in an incubator with 5% by volume $CO_2$ with a high atmospheric humidity.

Logarithmically growing cells were harvested by mild trypsinisation and 4,000 cells were added to a microtitre plate with 96 wells (Costar). The plates were incubated for one night in 5% by volume $CO_2$ at 37° C. to allow the cells to adhere to the plate. The cells were then treated with the platinum complex or cis-platinum and incubated for 72 hours. The plates were turned over and shaken to remove the media, pharmacologically active compounds and cells which had become loose. Formalin (10%) in a phosphate-buffered physiological saline solution was added and the cells were fixed for 10 minutes. The fixative is removed and the plates are dried in air, coloured for 15 minutes with 0.0075% by weight crystal violet, washed twice and dried in air. The spot was rendered soluble with 0.2 ml 0.1M acetic acid/ethanol (1:1) and the optical densities are determined with the aid of a Dynatech MR 600 microtitre plate reader. The $IC_{50}$ values (the concentration in mcg/ml which causes 50% inhibition of the cell growth) were calculated with the aid of linear regression analysis of the absorption data.

The results of the in vitro cytotoxicity tests are given in Table A. The compound in question is cytotoxic for all five cell lines. However, the most important fact is that the sub-lines of A2780 human ovary carcinoma (A2780/124 and A2780/DDP) which are resistant to cis-platinum are not able to withstand the present compound, as can be seen from the $IC_{50}$ ratios $\geq 4.0$.

Activity Against L1210 Murine Leukaemia

The platinum complex was investigated for anti-tumour action against L1210 murine leukaemia. $CDF_1$ mice with a weight of 20 g were inoculated intraperitoneally with $10^6$ ascitic cells of L1210 leukaemia. The administration of the active complex was started the day following the intraperitoneal implantation of the tumour. The complex was administered in diverse amounts by intraperitoneal injections. Groups of 6 mice were used for each dose and they were treated with a single dose of the complex on the treatment day. A group of ten control mice treated with a physiological saline solution was included in the experiment. Mice treated with cis-diamine-dichloro-platinum (cis-platinum) were included as positive comparisons. The mice were weighed before the treatment and again on the fifth or sixth day and the average change in weight was taken as a measure of the toxicity. The animals were assessed daily for mortality and the experiments were ended after 30 days. The tumour activity was determined on the basis of % T/C, which is the ratio of mean survival time of the group treated with the active complex relative to the mean survival time of the control group treated with a physiological saline solution times 100. The mice treated with physiological saline solution usually have a mean survival time of 7 days. A compound is regarded as active when this gives a T/C $\geq 125\%$.

Table B contains a summary of the assessment of the complex for the anti-tumour action against L1210 murine leukaemia. The % T/C values which are obtained for each dose examined are indicated. The compound in question (TNO-40) is active at all doses investigated, the maximum T/C being 193% at a dose of 4 mg/kg.

Action Against B16 Malenoma

The active compound (TNO-40) is evaluated for the anti-tumour action against B16 melanoma. $BDF_1$ mice, 10 per group, are inoculated intraperitoneally with 0.5 ml of a 10% (weight/vol) homogeneous tissue suspension of B16 melanoma. Intraperitoneal treatment with the active compound was started one day after the implantation and continued daily for a total of 9 days. The control group treated with a physiological saline solution and groups treated with cis-platinum were included in each experiment. The mice were assessed daily for survival and tests were stopped after 60 days. The mean survival time of the mice treated with the active agent relative to that of the comparison (% T/C) was used as a measure for the anti-tumour action. A compound is regarded as active with a % T/C of 125%.

The results of the tests on the metal complexes are summarized in Table C, in which % T/C which is achieved with each dose is indicated. The present compound is active at 0.4, 0.8 and 1.6 mg/kg per injection, with a maximum % T/C of 163% at a dose of 0.8 mg/kg per injection.

Action Against M5076 Reticulum Cell Sarcoma

The complex was also assessed for anti-tumour action against subcutaneously implanted M5076 sarcoma. $BDF_1$ mice, 8 per group, were inoculated subcutaneously with a fragment of a M5076 tumour. The mice were treated intravenously starting 5 days after the implantation and again on days 9, 13 and 17. Therefore a total of four treatments. Four doses of the complex were tested. A comparison group treated with physiological saline solution and groups treated with cis-platinum are included in this experiment. The mice were assessed daily for survival and the tests were ended after 75 to 80 days. The anti-tumour action was determined on the basis of (a) mean survival time of the mice treated with the active compound relative to that of the untreated mice (% T/C) and (b) the mean time for subcutaneously implanted tumours to reach a weight of 1 gram in mice treated with active compound relative to untreated mice (T-C). A compound is regarded as active if this gives a T/C $\geq 125\%$ or is T-C $\geq 13$ days.

The results of the tests with the platinum complex are summarized in Table D in which the percentage T/C and T-C for each dose tested is shown. The compound in question is active at 3 and 4 mg/kg per injection and gives % T/C values of 126 and 125% respectively and T-C values of 16.8 and 20.3 days.

TABLE A

| | In vitro cytotoxicity $IC_{50}$ (mcg/ml) | | | | |
|---|---|---|---|---|---|
| Compound | B16-F10 | HCT116 | A2780 | A2780/124 (ratio)[a] | A2780/DDP (ratio)[a] |
| Cis-platinum | 9.8 | 8.5 | 2.3 | 23 (10) | 28 (12.6) |
| TNO-40 | 7.4 | 16 | 6.4 | 21 (3.3) | 23 (3.6) |

[a] Ratio = $\dfrac{IC_{50}\ A2780/124}{IC_{50}\ A2780}$ or $\dfrac{IC_{50}\ A2780/DDP}{IC_{50}\ A2780}$

TABLE B

Inhibition of L1210 murine leukaemia

| Compounds | Dose= | % T/C |
|---|---|---|
| Cis-platinum | 4 | 131 |
| | 6 | 138 |
| | 8 | 131 |
| | 10 | 138 |
| TNO-40 | 2,5 | 179 |
| | 4 | 193 |
| | 6 | 186 |
| | 8 | 180 |

= Dose is mg/kg administered i.p., once on day 1.

TABLE C

Inhibition of B16 Melanoma

| Compounds | Dose= | % T/C |
|---|---|---|
| Cis-platinum | 0.4 | 117 |
| | 0.8 | 137 |
| | 1.6 | 171 |
| | 2.4 | 146 |
| TNO-40 | 0.2 | 127 |
| | 0.4 | 137 |
| | 0.8 | 163 |
| | 1.6 | 139 |

TABLE C-continued

Inhibition of B16 Melanoma

| Compounds | Dose= | % T/C |
|---|---|---|
| | 2.4 | 83 |

= Dose is mg/kg per injection administered i.p. on day 1-9

TABLE D

Inhibition of M5076 Sarcoma

| Compound | Treatment route | Dose= | % T/C | T-C (days) |
|---|---|---|---|---|
| Cis-platinum | iv | 3 | 134 | 18.3 |
| | | 4 | 135 | 16.3 |
| | | 5 | 131 | 20.5 |
| | | 6 | 121 | 20 |
| TNO-40 | iv | 3 | 126 | 16.8 |
| | | 4 | 125 | 20.3 |
| | | 5 | toxic | |
| | | 6 | toxic | |

= Dose is mg/kg administered i.v. on day 5, 9, 13 and 17

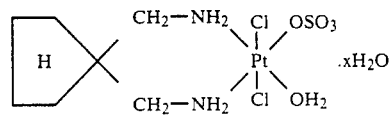

We claim:

1. Platinum-(IV)-diamine complex having the formula: